United States Patent [19]

Porter et al.

[11] 4,006,249
[45] Feb. 1, 1977

[54] SYSTEMIC TREATMENT OF PSORIASIS

[75] Inventors: William R. Porter, Etobicoke; John K. McKenzie; Paul A. Mitenko, both of Winnipeg, all of Canada

[73] Assignee: American Home Products Corporation, New York, N.Y.

[22] Filed: Aug. 6, 1975

[21] Appl. No.: 602,603

[52] U.S. Cl. .............................................. 424/326
[51] Int. Cl.$^2$ ..................................... A61K 31/155
[58] Field of Search .................................. 424/326

[56] References Cited

UNITED STATES PATENTS

| | | | |
|---|---|---|---|
| 3,383,409 | 5/1968 | Bream et al. | 424/326 |
| 3,591,636 | 7/1971 | Houlihan et al. | 424/326 |

FOREIGN PATENTS OR APPLICATIONS

| | | |
|---|---|---|
| 722,109 | 4/1969 | Belgium |
| 722,136 | 4/1969 | Belgium |

OTHER PUBLICATIONS

Merck Manual 12th Edition, (1972), pp. 1473–1475.

*Primary Examiner*—Norman A. Drezin
*Attorney, Agent, or Firm*—Stephen I. Miller; Robert Wiser

[57] ABSTRACT

A process for the treatment of psoriasis by systemic administration of 2,6-dihalobenzylideneaminoguanidines is disclosed.

9 Claims, No Drawings

SYSTEMIC TREATMENT OF PSORIASIS

BACKGROUND OF THE INVENTION

Psoriasis is a disease of the skin, whose etiology is unknown. The skin lesions associated with psoriasis may be described as dull red patches or plaques of scaly erythema. The scales are distinctive, having a slightly opalescent silvery appearance. The disease has a predilection for certain areas of the body; thus the scalp, the extensor surfaces of the extremities (particularly at the elbows and knees), the back and the buttocks are most usually affected. However, the nails, eyebrows, axillae, umbilicus and anogenital regions are also frequent cites of involvement.

To date, there has been no report of a complete and permanent cure for psoriasis, and although the several treatments of choice available afford temporary remission of the symptoms, recurrence is almost certain. Most treatments involve the topical application of steroid (e.g. the adrenocortical steroids) ointments and creams, and no clinically successful, long-term, systemic treatment for the disease is currently available.

The compounds utilized in the process of the invention, substituted benzylideneaminoguanidines and their pharmacologically acceptable acid addition salts, have previously been described in the literature. For example, Belgian Patents 722,109 and 722,136 disclose pharmaceutical compositions containing these compounds which are hypotensive, antibacterial, CNS active, analgesic, diuretic, and antiinflammatory agents; and British Patent 1,019,120 discloses the use of these compounds as herbicidal agents. In addition the preparation of the substituted benzaldehydes from which the benzylideneaminoguanidines of the invention may be prepared is described in Chemical Abstracts, 26, 1271 (1931); 31, 3816 (1936).

SUMMARY OF THE INVENTION

The invention sought to be patented in a principal process aspect resides in the concept of a process for treating a human being suffering from psoriasis which comprises administration of an effective amount of a compound of the formula:

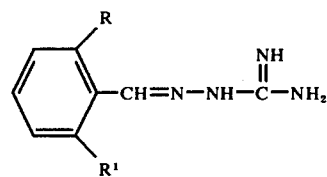

wherein R and R¹ are independently chlorine and fluorine, and the pharmacologically acceptable acid addition salts thereof.

The invention sought to be patented in its first subgeneric process aspect resides in the concept of a process for treating a human being suffering from psoriasis which comprises administration of an effective amount of the compound of the formula:

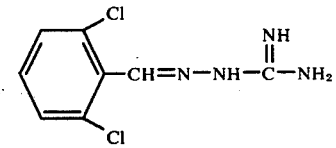

and the pharmacologically acceptable acid addition salts thereof.

The invention sought to be patented in its second subgeneric process aspect resides in the concept of a process for treating a human being suffering from psoriasis which comprises administration of an effective amount of the pharmacologically acceptable salt of the formula:

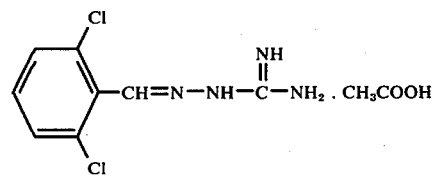

The invention sought to be patented in its third subgeneric process aspect resides in the concept of a process for ameliorating the clinical manifestations of psoriasis in a human being suffering from psoriasis which comprises administration of an effective amount of a compound of the formula:

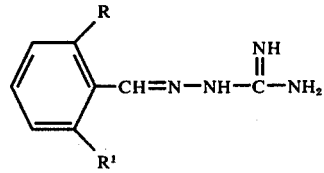

wherein R and R¹ are independently chlorine and fluorine, and the pharmacologically acceptable acid addition salts thereof.

The invention sought to be patented in its fourth subgeneric process aspect resides in the concept of a process for ameliorating the clinical manifestations of psoriasis in a human being suffering from psoriasis which comprises administration of an effective amount of the compound of the formula:

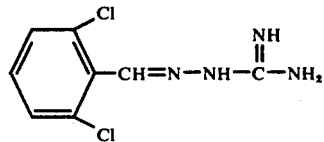

and the pharmacologically acceptable acid addition salts thereof.

The invention sought to be patented in its fifth subgeneric process aspect resides in the concept of a process for ameliorating the clinical manifestations of psoriasis in a human being suffering from psoriasis which comprises administration of an effective amount of pharmacologically acceptable salt of the formula:

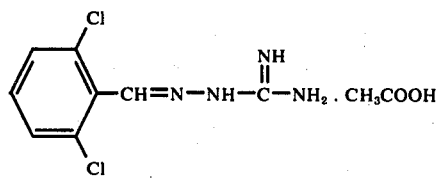

The invention sought to be patented in its sixth subgeneric aspect resides in the concept of a process for decreasing the psoriatic scaling experienced by a human being suffering from psoriasis which comprises administration of an effective amount of a compound of the formula:

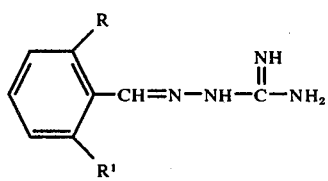

wherein R and $R^1$ are independently chlorine and fluorine, and the pharmacologically acceptable acid addition salts thereof.

The invention sought to be patented in its seventh subgeneric process aspect resides in the concept of a process for decreasing the psoriatic scaling experienced by a human being suffering from psoriasis which comprises administration of an effective amount of the compound of the formula:

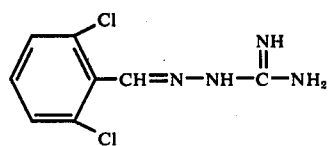

and the pharmacologically acceptable acid addition salts thereof.

The invention sought to be patented in its eighth subgeneric process aspect resides in the concept of a process for decreasing the psoriatic scaling experienced by a human being suffering from psoriasis which comprises administration of an effective amount of the pharmacologically acceptable salt of the formula:

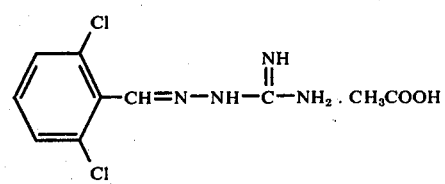

The invention sought to be patented in its ninth subgeneric aspect resides in the concept of a process for decreasing the psoriatic erythema experienced by a human being suffering from psoriasis which comprises administration of an effective amount of a compound of the formula:

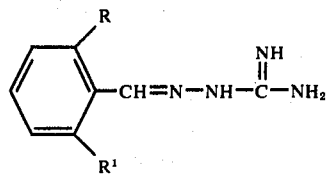

wherein R and $R^1$ are independently chlorine and fluorine, and the pharmacologically acceptable acid addition salts thereof.

The invention sought to be patented in its tenth subgeneric process resides in the concept of a process for decreasing the psoriatic erythema experienced by a human being suffering from psoriasis which comprises administration of an effective amount of the compound of the formula:

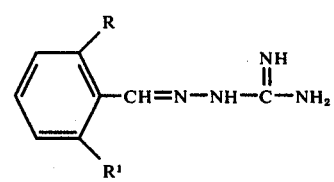

and the pharmacologically acceptable acid addition salts thereof.

The invention sought to be patented in its eleventh subgeneric process aspect resides in the concept of a process for decreasing the psoriatic erythema experienced by a human being suffering from psoriasis which comprises administration of an effective amount of the pharmacologically acceptable salt of the formula:

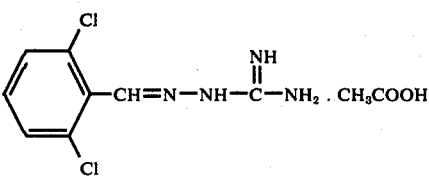

DESCRIPTION OF THE INVENTION

The present invention provides a process whereby a human being suffering from psoriasis is treated systemically for the disease with a compound of the formula:

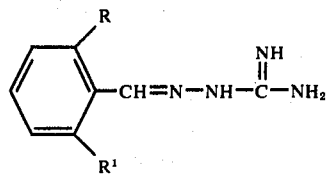

wherein R and $R^1$ are independently chlorine and fluorine, and the pharmacologically acceptable acid addition salts thereof.

For reasons of convenience, the hereinafter disclosed teaching of the practice of the process of the invention will be described by utilizing a specific embodiment of the invention. This specific embodiment, 2,6-dichlorobenzylideneaminoguanidine has been given the generic name guanabenz. This limitation is made for convenience and clarity in describing the invention and is not meant to delimit the scope of the invention as herein disclosed and hereinafter claimed.

Guanabenz is currently undergoing clinical trial as an antihypertensive agent. It is an effective antihypertensive agent, and has not been observed to significantly affect blood pressure in a normotensive individual. Thus, the use of guanabenz by a normotensive individual suffering from psoriasis would not be contraindicated.

When used herein, the term "treating" means the systemic administration to a person suffering from psoriasis, of a compound of the formula:

wherein R and R[1] are independently chlorine and fluorine and the pharmacologically acceptable acid addition salts thereof. As a result of the systemic administration of a compound or salt of the above formula a remission of the symptoms of the psoriatic patient, in most cases, will result. Thus, one affected by psoriasis can expect a decrease in scaling, erythema, size of the plaques, pruritis and other symptoms associated with psoriasis. The dosage of medicament and the length of time required for successfully treating each individual psoriatic patient may vary, but those skilled in the art of medicine will be able to recognize these variations and adjust the course of therapy accordingly.

The compounds of the process of the invention can be prepared and administered in a wide variety of oral and parenteral dosage forms.

For preparing compositions from the compounds described by this invention, inert, pharmacologically-acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet-disintegrating agents; it can also be an encapsulating material. In powders the carrier is finely divided solid which is in admixture with the finely divided compound. In the tablet the compound is mixed with carrier having the necessary binding properties in suitable proportions and compacted in the shape and size desired. The powders and tablets preferably contain from 5 or 10 to 70 percent of the active ingredient. Suitable solid carriers are megnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "preparation" is intended to include the formulation of the compound with encapsulating material as carrier providing a capsule in which the compound (with or without other carriers) is surrounded by carrier, which is thus in association with it. Similarly, cachets are included. Tablets, powders, cachets, capsules can be used for oral administration.

Liquid form preparations include solutions, suspensions and emulsions. As an example may be mentioned water-propylene glycol solutions for parenteral injection. Liquid preparations can also be formulated in solution in aqueous polyethylene glycol solutions. Aqueous suspensions suitable for oral use can be made by dispensing the finely divided compound in water with viscous material, natural or synthetic gums, resins, etc., for example, gum arabic, ion-exchange resins, methyl cellulose, sodium carboxymethyl cellulose and other well-known suspending agents.

Preferably, the pharmacological preparation is in unit dosage form. In such form, the preparation is subdivided in unit doses containing appropriate quantities of the compound, the unit dosage form can be a packaged preparation, the package containing discrete quantities of preparation, for example, packeted powders of vials or ampoules.

The unit dosage form can also be a capsule, cachet or tablet itself or it can be the appropriate number of any of these in packaged form. The quantity of compound in a unit dose of preparation may be varied or adjusted from 1 mg. to 100 mg. according to the particular application and the potency of the active ingredient.

In therapeutic use as agents for treating psoriasis, the compounds utilized in the process of this invention are administered at the initial dosage of about 0.02 mg. to 1.0 mg. per kilogram daily. The dosages, however, may be varied depending upon the requirements of the patient and the compound being employed. Generally, treatment is initiated with smaller dosages which are less than the optimum dose of the compound. Thereafter, the dosage is increased by small increments until the optimum effect under the circumstances is reached. In general, the compounds of the invention are administered at a dosage level which will generally afford effective results without causing any harmful or deleterious side effects, and which is from about 0.02 mg. to about 1.0 mg. per kilogram per day. In particular, guanabenz [(2,6-dichlorobenzylidene)amino]guanidine which has been shown to possess particularly outstanding activity for the systemic treatment of psoriasis may be employed in humans at a range from about 2 mg. to about 50 mg. per patient per day, although as aforementioned variations will occur. However, a dosage level that is in the range of from about 8 mg. to about 32 mg. per patient per day is most desirably employed in order to achieve effective results. For convenience, the total daily dosage may be divided and administered in portions during the day if desired.

When used herein, the term pharmacologically acceptable acid addition salt, means the salt obtained by reacting a benzylideneaminoguanidine of the invention with a pharmacologically acceptable acid. Such acids will be familiar to those skilled in the art, e.g. acetic, hydrochloric, sulfuric, nitric, fumaric, and the like.

The following case histories describe the use of guanabenz by patients suffering from psoriasis:

CASE I

A 48 year old man suffering from psoriasis for the last 13 years, had nummular plaques were thick with silvery scales over his elbows, knees, and sacrum, and nummular lesions on his scalp. The anterior surfaces of his legs were covered with thick red lesions, some deep pustules on his palms and soles and his nails were disintegrating. After two weeks on placebo there was no change in his psoriasis. Active treatment was initiated and after two weeks taking guanabenz 8 mg. b.i.d. all lesions were improving, his hands were improved and were no longer cracking. The lesions across his legs, back, and chest were thinning and clearing in the center. His scalp was improved and there was no change in his nails.

CASE II

A 48 year old woman reported having psoriasis for twenty years. After a three week course of treatment with placebo, she still had thick white plaques on her scalp and the nape of her neck with scaly areas over her knees and elbows. She had an aggregate of guttate lesions around her waistline and under her breasts with the same on her legs and arms. She had few pits in her fingernails. After three weeks of therapy (guanabenz 8 mg. b.i.d.) there was no change in her skin. After three more weeks active therapy (including a two week vacation in the sun) her skin was generally better. After four more weeks of active therapy, the patient reported her skin improved during her vacation as it usually does but this time the lesions did not recurr, which had been her usual experience. In addition, her scalp was clear which usually did not improve in the sun.

At the end of three additional weeks active treatment, her condition was still clear and she was much better. At this time, active therapy was discontinued and placebo was administered. After four weeks her lesions had relapsed on her scalp, ears, abdomen and breasts.

CASE III

A 30 year old male with a lot of scaly plaques on his scalp. His elbows and knees had thick red scales. He had large plaques on the extension surfaces of his arms and legs with involvement of the uretogenital region and trunk. His nails were normal. After six weeks on placebo there was no change in his condition. After three weeks of active therapy (guanabenz 8 mg. b.i.d.) all lesions were much thinner and not as scaly and his scalp was improved. Active treatment was continued an additional eleven weeks at which time he was described as doing very well, his scalp was about clear and the lesions on his arms and legs were very thin, practically clear.

CASE IV

A 30 year old female reporting she had psoriasis for one year had the volar and extension surfaces of both arms covered with nummular and guttate plaques. She had a few nummular plaques on her scalp. She had lesions of the legs and trunk with no pits in her nails. There was no improvement in her condition during a three week course on placebo therapy. Afte six weeks on active therapy (guanabenz 8 mg. b.i.d.) she was tremendously better, her skin and scalp were practically clear with a little scale around her ankles. She showed no relapse on renewed placebo therapy.

CASE V

A 40 year old medical doctor reported having psoriasis for 21 years. He initiated active therapy, guanabenz 4 mg. b.i.d., and no change in his condition was noted after 8 days. He then increased the dose to 8 mg. b.i.d. and after 2 days noted a visible improvement in his psoriasis. After an additional six to eight weeks active therapy he reported that his skin lesions were better than they had been in years. At this time he discontinued taking the drug and after about four weeks noted the lesions becoming redder with more scaling. This continued for several weeks when the condition began to remit, which remission has continued.

The subject matter which the applicants regard as their invention is particularly pointed out and distinctly claimed as follows:

1. A process for ameliorating the clinical manifestations of psoriasis in a human suffering from psoriasis which comprises administering to said human an effective amount of a compound of the formula:

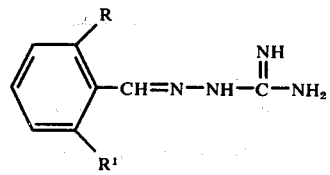

wherein R and $R^1$ are independently chlorine and fluorine, and the pharmacologically acceptable acid addition salts thereof.

2. The process of claim 1 wherein R and $R^1$ are chlorine.

3. The process of claim 2 wherein the pharmacologically acceptable acid is acetic.

4. A process for decreasing the psoriatic scaling experienced by a human suffering from psoriasis which comprises administering to said human effective amount of a compound of the formula:

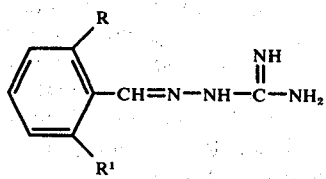

wherein R and $R^1$ are independently chlorine and fluorine, and the pharmacologically acceptable acid addition salts thereof.

5. The process of claim 4 wherein R and $R^1$ are chlorine.

6. The process of claim 5 wherein the pharmacologically acceptable acid is acetic.

7. A process for decreasing the psoriatic erythema experienced by a human suffering from psoriasis which comprises administering to said human an effective amount of a compound of the formula:

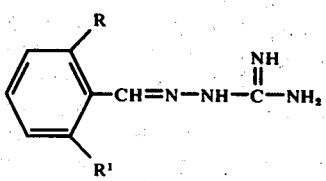

wherein R and $R^1$ are independently chlorine and fluorine, and the pharmacologically acceptable acid addition salts thereof.

8. The process of claim 7 wherein R and $R^1$ are chlorine.

9. The process of claim 8 wherein the pharmacologically acceptable acid is acetic.

* * * * *